United States Patent [19]

Belly et al.

[11] Patent Number: 5,093,239

[45] Date of Patent: Mar. 3, 1992

[54] REAGENTS FOR DETECTING OXIDASE POSITIVE MICROORGANISMS

[75] Inventors: Robert T. Belly, Webster; Lee J. Fleckenstein, Rochester; Drake M. Michno, Webster; William N. Washburn, Ionia, all of N.Y.

[73] Assignee: Eastman Kodak Company, Rochester, N.Y.

[21] Appl. No.: 188,999

[22] Filed: May 2, 1988

[51] Int. Cl.$^5$ .............................................. C12Q 1/04
[52] U.S. Cl. ...................................... 435/34; 435/25; 435/28; 435/29
[58] Field of Search ...................... 435/25, 28, 29, 34; 430/553, 554, 559, 561, 562, 958

[56] References Cited

U.S. PATENT DOCUMENTS

| | | | |
|---|---|---|---|
| 3,148,062 | 9/1964 | Whitmore et al. | 96/55 |
| 3,443,940 | 5/1969 | Bloom et al. | 96/3 |
| 4,248,962 | 2/1981 | Lau | 430/958 |
| 4,853,186 | 8/1989 | Mura et al. | 430/223 |
| 4,853,328 | 8/1989 | Okazaki et al. | 435/28 |

FOREIGN PATENT DOCUMENTS 0060518  7/1985  European Pat. Off. .

OTHER PUBLICATIONS

*Biochemical Tests for Identification of Medical Bacteria,* Second Edition, J. F. MacFiddin, Williams & Wilkins, p. 250.

*Primary Examiner*—Sam Rosen
*Attorney, Agent, or Firm*—John R. Everett

[57] ABSTRACT

Compounds and reagents containing the compounds are disclosed for detecting oxidase positive organisms. The compounds have the structure $$\text{-(COUP—LINK-)}_n\text{R}$$

wherein
COUP— represents a radical that couples with an oxidized primary aromatic amine and releases —LINK—R;
—LINK— represents a divalent radical that undergoes intramolecular cyclization and release of —R upon release by COUP—;
n represents zero or one;
—R represents a monovalent radical that forms a detectable species in the form of a colorimetric dye or fluorescent compound upon release from —LINK—; wherein —R is selected from the group consisting of:

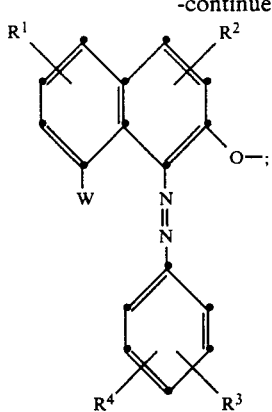

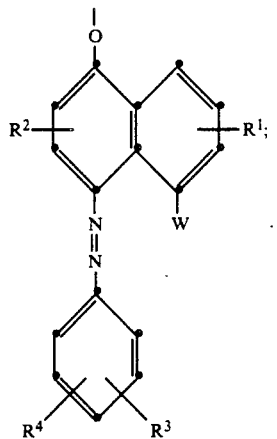

; and wherein
- W represents hydrogen; halogen; hydroxy; substituted or unsubstituted carbonamido; sulfonamido; sulfonyl; ureido or amino;
- $R^1$ and $R^2$ each independently represent hydrogen, halogen, alkyl, alkoxy, carboxy, sulfo, cyano, nitro, carboxylic acid ester, carbonyl, sulfonyl, carbonamido, sulfonamido, alkylsulfonyl, arylsulfonyl; and
- $R^3$ and $R^4$ each independently represent halogen, nitro, sulfonamido, sulfonyl, carbonamido, carbonyl, cyano, alkylsulfonyl, arylsulfonyl;
- $R^6$ represents H, $CH_3$ or $C_2H_5$;
- $X_5$ represents —O—, —S— or $$-\overset{|}{N}R^5;$$

and
R$^5$ represents H, alkyl, cycloalkyl or aryl.

The reagnets containg also a hydrogen donating primary amine.

3 Claims, No Drawings

REAGENTS FOR DETECTING OXIDASE POSITIVE MICROORGANISMS

FIELD OF THE INVENTION

The present invention relates to novel compounds and their use as reagents in methods and elements for detecting oxidase positive organisms.

BACKGROUND OF THE INVENTION

Dye forming reactions are used in the oxidase test for detection of oxidase-positive organisms.

The oxidase test is based on the bacterial production of an intracellular oxidase enzyme. See *Biochemical Tests for Identification of Medical Bacteria*, p. 250, J. MacFaddin, Williams and Wilkins Co. Oxidase-positive organisms include Pseudomonadaceae, Moraxella, Nesseria, Aeromonas, Vibrionaceae and *Pleisiomonas shigelloides*.

Oxidase-positive organisms produce reduced cytochrome c oxidase. It is oxidized in the presence of oxygen. Oxidized cytochrome c oxidase oxidizes primary amines such as dimethyl-p-phenylenediamine which in turn reacts with α-napththol to form indophenol blue. The formation of indophenol blue signals the presence of an oxidase-positive organism.

The reaction of oxidized dimethyl-p-phenylenediamine and α-napththol, however, provides a relatively insensitive test and the resulting dye is unstable, thus failing to indicate the presence of oxidase-positive organism in some cases.

SUMMARY OF THE INVENTION

The present invention provides a reagent comprising:
a) a hydrogen donating primary amine; and
b) a compound selected from those having the general formula

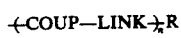

wherein
COUP— represents a radical that couples with an oxidized primary aromatic amine and releases —LINK—R;
—LINK— represents a divalent radical that undergoes intramolecular cyclization and release of —R upon release by COUP—;
n represents zero or one;
—R represents a monovalent radical that forms a detectable species in the form of a colorimetric dye or fluorescent compound upon release from —LINK—;

wherein —R is selected from the group consisting of:

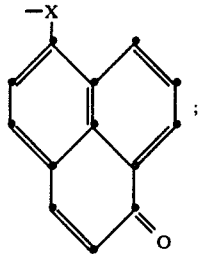

-continued

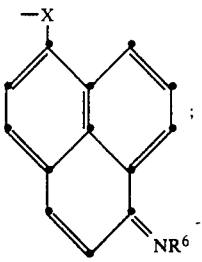

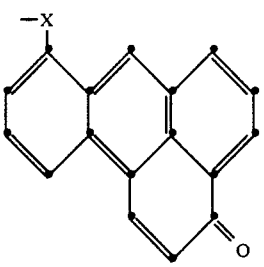

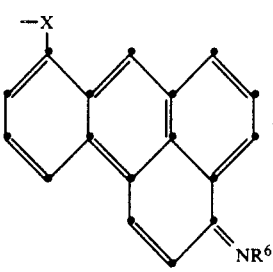

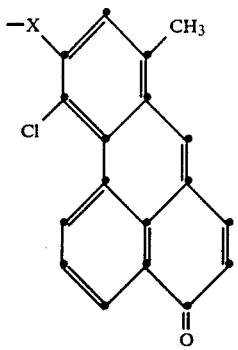

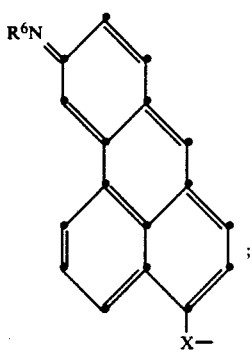

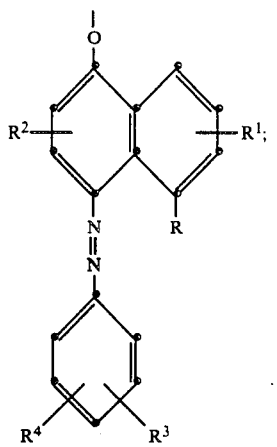

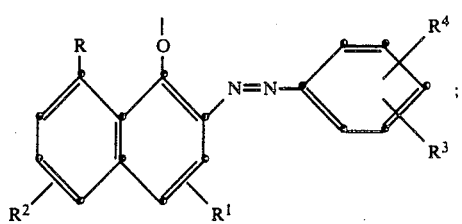

and

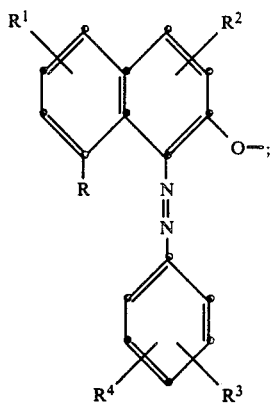

wherein

R represents hydrogen, halogen such as chloro or bromo; hydroxy; or substituted or unsubstituted carbonamido such as acetamido or sulfonamido; sulfonyl, ureido or amino;

$R^1$ and $R^2$ each independently represent hydrogen, halogen, alkyl such as methyl, ethyl or propyl, alkoxy such as methoxy, t-butoxy, carboxy, sulfo, cyano, nitro, carboxylic acid ester, carbonyl, sulfonyl, carbonamido, sulfonamido, alkylsulfonyl such as methanesulfonyl, arylsulfonyl such as benzenesulfonyl; and $R^3$ and $R^4$ each independently represent halogen, nitro, sulfonamido, sulfonyl, carbonamido, carbonyl, cyano, alkylsulfonyl such as methanesulfonyl, and arylsulfonyl such as benzenesulfonyl;

$R^6$ represents H, $CH_3$ or $C_2H_5$;

X represents —O—, —S— or 

and $R^5$ represents H, alkyl such as methyl, ethyl or butyl, cycloalkyl such as cyclohexyl or aryl such as phenyl or napthyl.

The compounds COUP-(-LINK-)-R combine with hydrogen- donating primary amines (referred to as amine hereinafter) to form reagents which, in the presence of oxidase positive organisms, release a reporter compound in the form of (1) colorimetric dyes having high extinctions and absorptions at wavelengths greater than 500 mm or (2) fluorescent dyes having absorptions and emissions above 500 mm and low pKa values, i.e. about 6, so they exhibit maximum fluorescence in the physiological pH range of 6-9.

DETAILS OF THE INVENTION

The compounds, covered by the general formula COUP-(-LINK-)$_n$R, fall into two general groups.

Group I include those in which n represents zero. In these compounds —R is linked directly to COUP— without the intervening linking group —LINK—. —R is directly released in the presence of an oxidized amine and forms the detectable species.

Group II include those compounds in which n equals 1. These compounds are anchimeric releasing couplers. This means that in the presence of an oxidized amine, the —LINK—R portion is released from COUP— and undergoes an intramolecular reaction to form a heterocyclic ring with concomitant release of —R to form the detectable species.

In both groups of compounds, couplers are known in the photographic arts from which the COUP— component may be easily made. COUP— radicals are disclosed, for example in European Patent Application 0 060 518; U.S. Pat. Nos. 3,443,940 and 3,148,062.

The compounds of group I are formed using such known couplers by reacting the latter with compounds containing —R. In general, the reaction is carried out using any of the techniques known in the photographic arts for forming dye releasing couplers. Such methods are exemplified for example, in European Patent Application 0 060 518.

The compounds of group II include the linking group —LINK— between the —R and COUP—. The compounds of this group utilize the same COUP— radicals used in group I. Representative linking groups include:

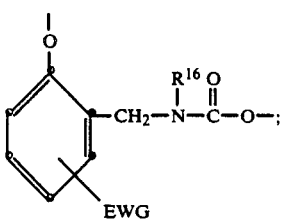

-continued

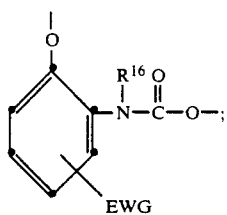

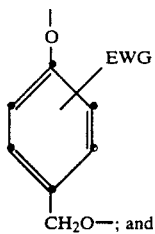

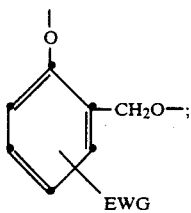

wherein $R^{16}$ represents $CH_3$, $C_2H_5$, n—$C_3H_7$ or i—$C_3H_7$;

EWG represents an electron withdrawing group in ortho or para position relative to the oxy group —O—, such as —$NO_2$, —$CO_2R^{17}$, —$SO_2R^{17}$, —$SO_2NR_2^{17}$ or —CN, wherein —$R^{17}$ represents H, alkyl such as methyl, ethyl or octadecyl; or aryl such as phenyl, tolyl or napthyl.

Preferred examples of —LINK— are:

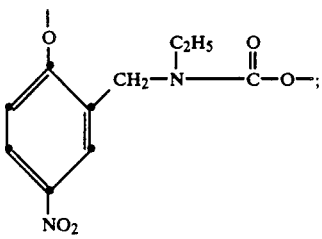

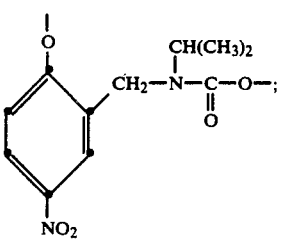

-continued

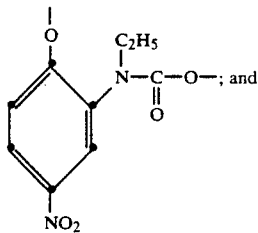

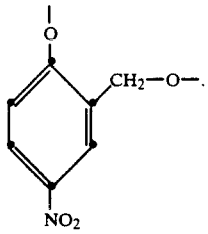

Other substituents can be present in the benzene ring provided they do not adversely affect the rate of coupling or cyclization to release —R.

The anchimeric compounds of group II can be made by conventional methods used to make anchimeric dye releasing couplers of, for example, U.S. Pat. No. 3,443,940 or 3,148,062.

In general the compounds of groups I and II have structures similar to those disclosed in European Patent Application 0 060 518 and U.S. Pat. Nos. 3,148,062 and 3,443,940. However, —R, alone or together with —(LINK)—, makes the compounds novel.

Examples of the compounds from which COUP— radicals may be formed and which are useful in both group I and II compounds are as follows:

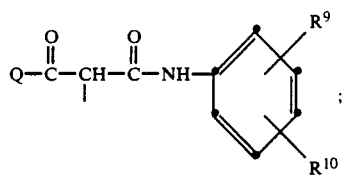

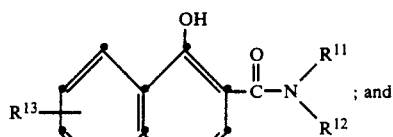

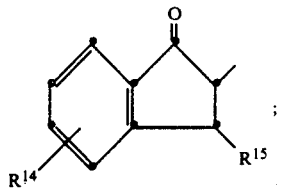

wherein

Q represents alkyl such as methyl, t-butyl or substituted or unsubstituted aryl such as phenyl, p-methoxyphenyl;

$R^9$ and $R^{10}$ each independently represent halogen such as chloro or fluoro, hydrogen, nitro, carboxy, sulfo, substituted or unsubstituted carbonamido or sulfonamido; or ureido;

$R^{11}$ and $R^{12}$ each independently represent hydrogen, alkyl such as methyl, ethyl or dodecyl, substituted or unsubstituted aryl such as phenyl or tetradecyloxyphenyl or dicarboxyphenyl;

$R^{13}$ represents hydrogen, halogen, carboxy, sulfo, alkyl such as methyl or ethyl, sulfonamido, carbonamido, etc.;

$R^{14}$ and $R^{15}$ each independently represent hydrogen, halogen such as chloro or fluoro, carboxy, sulfo, alkyl such as methyl, ethyl or hexadecyl, substituted or unsubstituted sulfonamido, carbonamido, etc.

Preferred examples of COUP— include:

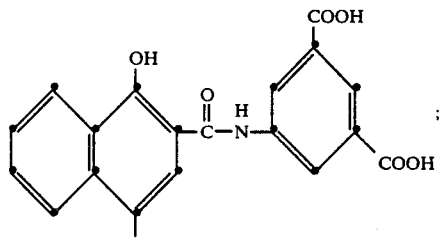

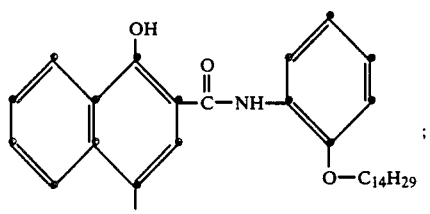

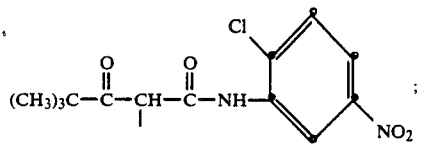

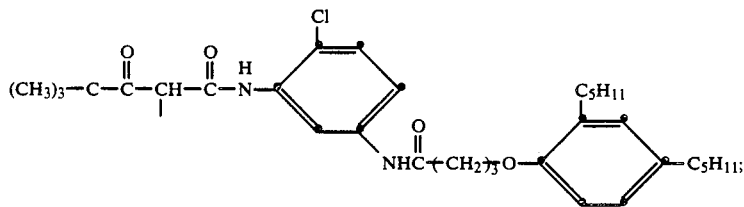

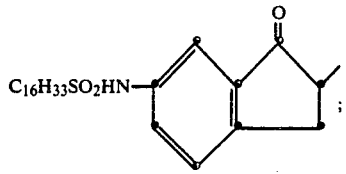

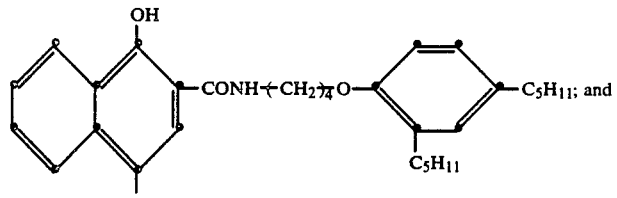

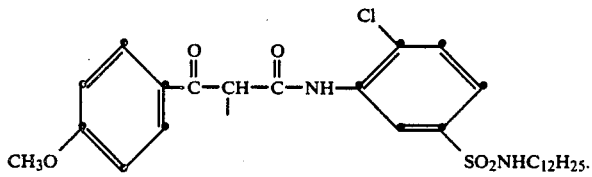

A portion of representative compounds according to group I are presented in Table I.
TABLE I
1) 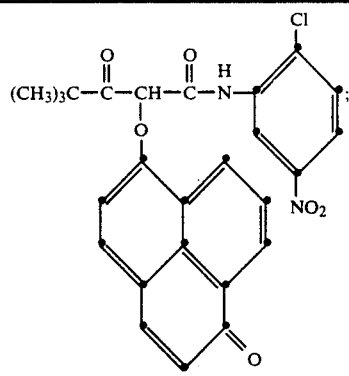
2) 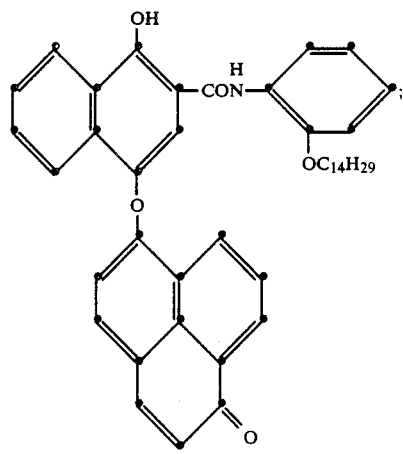
3) 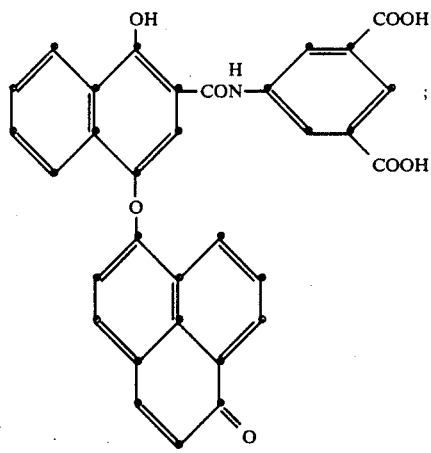
4) 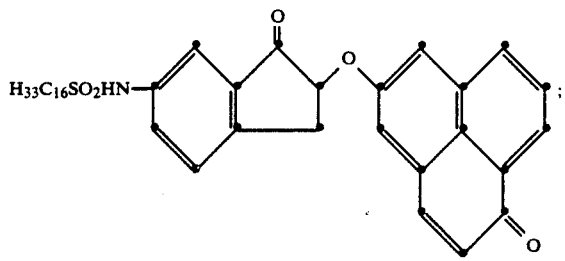
and TABLE I-continued
5)
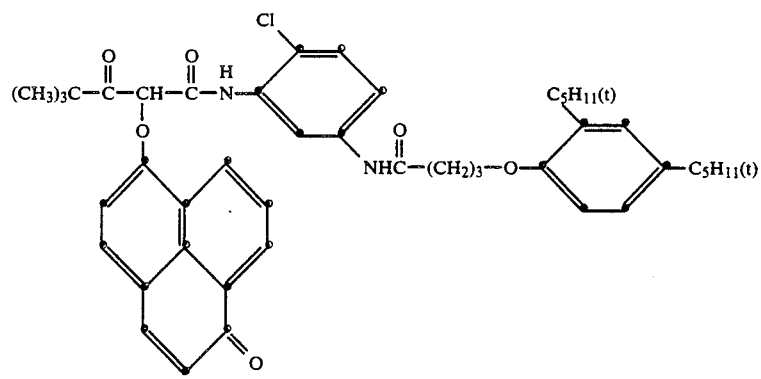
A portion of the representative anchimeric compounds of group II of the invention are as follows:
TABLE II
1)
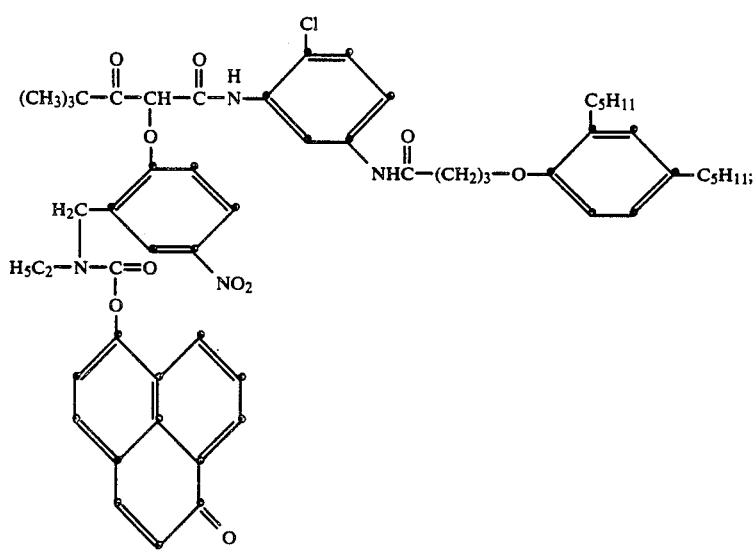

TABLE II-continued
2)
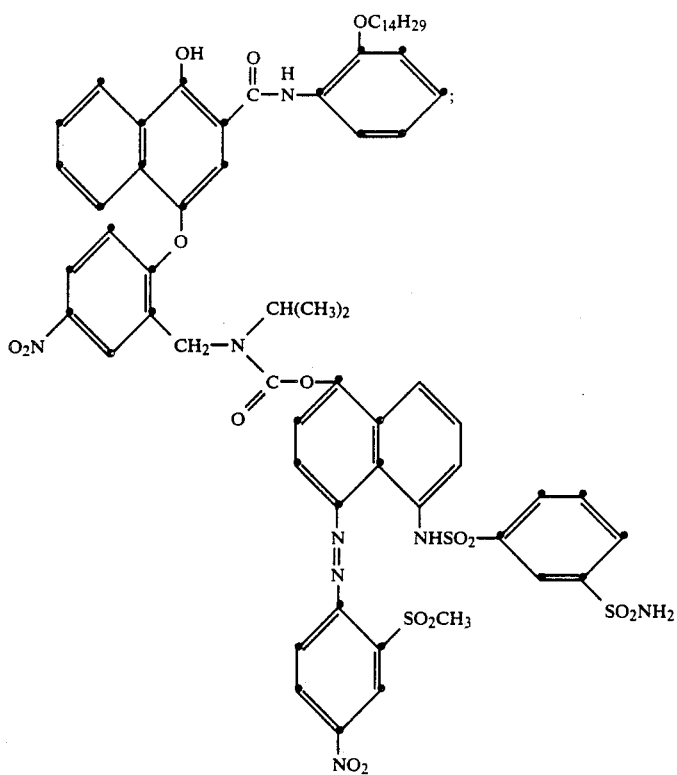
3)
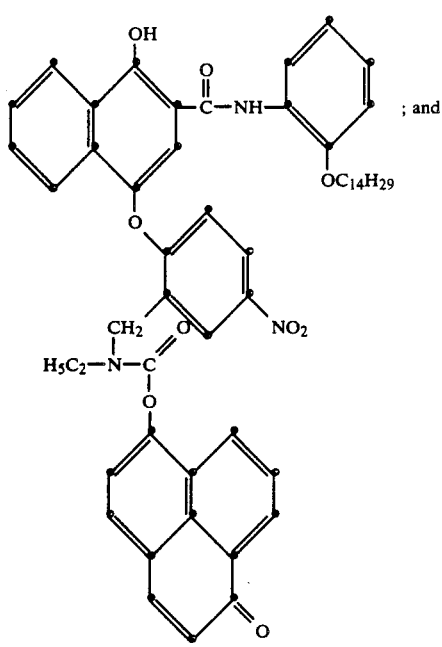
; and

TABLE II-continued

4) 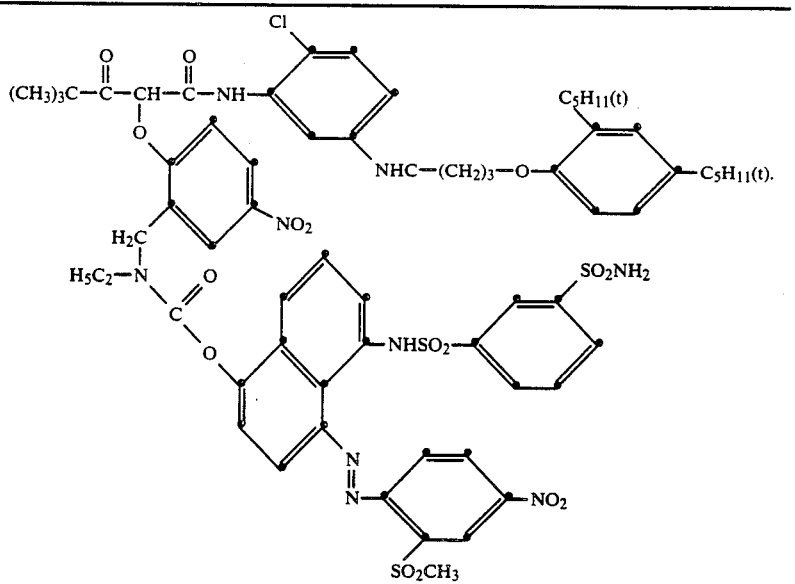

The hydrogen donating primary amines which are useful in this invention are those compounds designated as developers in the photographic arts. Such amines include p-phenylenediamines, p-aminophenols and pyrazolidones. A portion of representative amines are presented in Table III.

TABLE III

1) 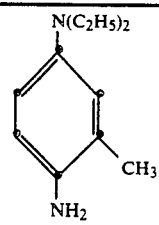 ;

2) 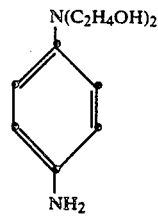 ;

3) 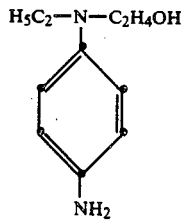 ;

4) 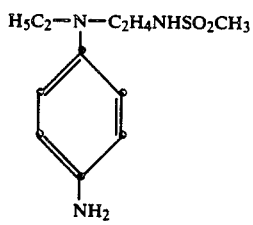 ;

TABLE III-continued

5) 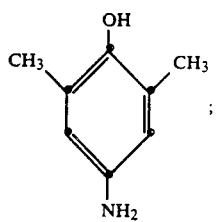 ;

6) 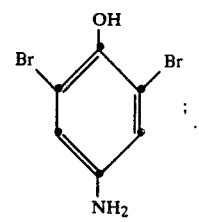 ;

7) 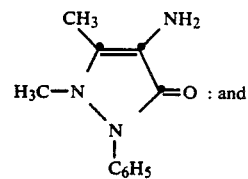 : and

8) 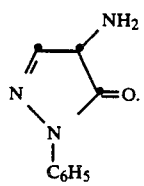 .

Detection of oxidase positive organisms is carried out simply by contacting a material, such as an aqueous solution, suspected of containing the organism with a reagent of the invention. The reagent is prepared by dissolving the COUP-(-LINK-)-R compound primary amine in an organic solvent. The relative amounts of each material in the reagent and the choice of solvent are not critical. Anyone skilled in the art will be able to establish the amount of the reagent needed to carry out detection.

The method of this invention can be practiced with a dry analytical element. A variety of different elements, depending on the method of assay, can be prepared in accordance with the present invention. Elements can be configured in a variety of forms, including elongated tapes of any desired width, sheets, slides or chips. The simplest element can be composed of an absorbent carrier material or water soluble polymer, for example, a thin sheet of a self-supporting absorbent or bibulous material, such as filter paper or strips, which contains the dyes of this invention. A useful element is discussed in commonly owned U.S. Ser. No. 045,937 filed May 4, 1987 by Burdick et al. The element comprises a water soluble polymer in which a reagent is included.

The elements can also have two or more discrete zones, either in the same layer or superimposed. At least one of the zones can be a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass or be transported between superposed regions of adjacent zones. In other words, when the element is contacted with fluid, all reagents of the analytical composition become mixed and can readily move within the element as a composition. Preferably, each zone is a separately coated layer, although two or more zones can be separate areas in a single layer of the element. Besides the references noted above, suitable element components are described also, for example, in U.S. Pat. Nos. 4,042,335 (issued Aug. 16, 1977 to Clément), 4,132,528 (issued Jan. 2, 1979 to Eikenberry et al), and 4,144,306 (issued Mar. 13, 1979 to Figueras).

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), 4,270,920 (issued June 2, 1981 to Kondo et al) and 4,312,834 (issued Jan. 26, 1982 to Vogel et al).

The absorbent carrier material can be a porous spreading zone. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters, polycarbonates, cellulose esters and others known in the art.

The porous spreading zone can be prepared from any suitable fibrous or non-fibrous material or mixtures of either or both. The void volume and average pore size of this zone can be varied depending upon the use intended.

Useful spreading zones can be prepared using fibrous materials, either mixed with a suitable binder material or woven into a fabric, as described in U.S. Pat. No. 4,292,272 (issued Sept. 29, 1981 to Kitajima et al), polymeric compositions or particulate materials, for example, beads bound together with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760. It is desirable that the spreading zone be isotropically porous, meaning that the porosity is the same in each direction in the zone as caused by interconnected spaces or pores between particles, fibers or polymeric strands.

The assay method can be manual or automated. In general, in using the dry elements, a determination is made by taking an element from a supply roll, chip packet or other source and physically contacting it with a sample (for example, up to 200 $\mu$l) of the liquid to be tested so that the sample and reagents within the element become mixed. Such contact can be accomplished in any suitable manner, for example, by dipping or immersing the element into the sample or, preferably, by spotting the element by hand or machine with a drop of the sample with a suitable dispensing means.

The following examples illustrate the utility of the reagent of the invention in detecting oxidase positive organisms.

EXAMPLE 1

Assay for *Pseudomonas aeruginosa*

This example compares the detection of *Pseudomonas aeruginosa* (an oxidase-positive organism) and *Escherichia coli* (an oxidase-negative organism) using dye releasing Compound 1 of Table I which releases a fluorescent dye.

A dispersion of the Compound 1 was prepared as follows. Compound 1 (4 mg) was dissolved in N,N-dimethylformamide (DMF, 250 $\mu$L). A surfactant, Triton X-100 (500 $\mu$L), was added. The solution was mixed and added slowly with stirring to 25 mL of 0.05M potassium phosphate buffer (pH 7.5).

*Escherichia coli* (*E. coli*) was grown overnight in brain heart infusion (BHI) broth at 37° C. without shaking. *Pseudomonas aeruginosa* (*P. aeruginosa*) was also grown overnight in BHI broth at 37° C. with shaking. About 40 mL of each culture growth was centrifuged, decanted, washed with KP buffer, and suspended in buffer, such that 75 $\mu$L of cells in 3 mL buffer gave an OD at 620 nm of 0.448.

The assay was run as follows:

A reagent of the invention was prepared from the Compound 1 dispersion (1 mL), a primary amine, 4-amino-3-methyl-N,N-diethylaniline (25 $\mu$L of a 50 mg/mL methanol solution). The reagent was mixed with *P. aeruginosa* (100 $\mu$L) and the buffer, to a final volume of 3 mL.

A control solution was prepared in the same manner, except using *E. coli*. A background control solution was prepared containing the reagent without the organisms.

Fluorescence was then measured. Excitation was at 540 nm. Emission was at 620 nm. After 7 minutes, the solution containing *P. aeruginosa* (an oxidase-positive organism) showed a change in relative fluorescence of 52 units, while the *E. coli* (oxidase-negative) showed a change of only 5 units. The background control showed a change of 12 units, due to aerial oxidation of the developer.

EXAMPLE 2

Assay for *Pseudomonas aeruginosa*

This example compares the detection of *P. aeruginosa* (oxidase-positive organism) and *E. coli* (oxidase-negative organism) using the anchimeric dye releasing Compound 1 of Table II which releases a fluorescent dye.

*P. aeruginosa* and *E. coli* were grown as described in Example 1. Each were made to a concentration such that 50 μL of cells in a 3 mL cuvette gave an OD at 620 nm of 0.1 unit.

A dispersion of Compound 2 was prepared as described in Example 1 for Compound 1. A test solution was prepared from the dispersion (1 mL), the primary amine of Example 1 (25 μL), *P. aeruginosa* (50 μL), and the buffer (1.9 mL). A control solution was prepared as in Example 1 using *E. coli*. A background control containing all the reagents except organisms was also prepared.

Fluorescence was measured at excitation 540 nm and emission 620 nm. After 10 minutes, the background control and *E. coli* control showed very little increase in fluorescence. However, the test solution showed a large increase in fluorescence.

EXAMPLE 3

Assay for *Pseudomonas aeruginosa*

This example compares the detection of *P. aeruginosa* (oxidase-positive organism) and *E. coli* (oxidase-negative organism) using anchimeric Compound 2, Table II, which releases a cyan dye.

*E. coli* was grown according to Example 1 and suspended in buffer, such that 100 μL of cells in 3 mL of buffer gave an OD at 620 nm of 0.135. *P. aeruginosa* was grown according to Example 1 and suspended in buffer such that 75 μL of cells in 3 mL of buffer gave an OD of 0.135.

A dispersion was prepared by dissolving Compound 2, Table II (16 mg) in DMF (1 mL); 250 μL of this solution was mixed with Triton X-100 solution (0.5 mL) and the resulting solution added slowly to 25 mL of 0.05M of the buffer, pH 7.5.

A test solution was prepared from the Compound 2 dispersion (100 μL), the primary amine (25 μL), *P. aeruginosa* (75 μL) and the buffer (200 μL).

A control solution was prepared in the same manner, except using *E. coli* (100 μL). A background control contained all reagents except organisms.

The optical density (OD) was measured at 37° C. at 635 nm, and the change in OD was determined after 10 minutes. The OD for *P. aeruginosa* (oxidase-positive organism) was 1.224. The OD for the *E. coli* control was 0.211 and the background control was 0.266.

EXAMPLE 4

Assay for *Pseudomonas aeruginosa* with Reagents Coated in a Dry Element

A poly(ethylene terephthalate) support was coated at about pH 6 with a layer comprising surfactant Zonyl FSN, 4-amino-3-methyl-N,N-diethylaniline, Compound 3, Table I and poly(acrylamide-co-N-vinylpyrrolidone), 90:10.

A portion of this element (~1 cm²) was added to a solution containing 3 mL of potassium phosphate buffer, 0.05M, pH 7.5 and 100 μl of *Pseudomonas aeruginosa* solution. A second portion of the element was added to a buffer solution without *Pseudomonas aeruginosa* cells for a background control.

Fluorescence was then measured at excitation 540 nm and emission 620 nm. After 10 minutes, the solution containing the *Pseudomonas aeruginosa* showed a large increase in fluorescence over the background control.

The invention has been described in detail with particular reference to preferred embodiments thereof, but it will be understood that variations and modifications can be effected within the spirit and scope of the invention.

We claim:

1. A reagent for detecting oxidase positive organisms comprising an amine selected from the group consisting of p-phenylenediamines, p-aminephenols and pyrazolidones; and a compound selected from the group consisting of

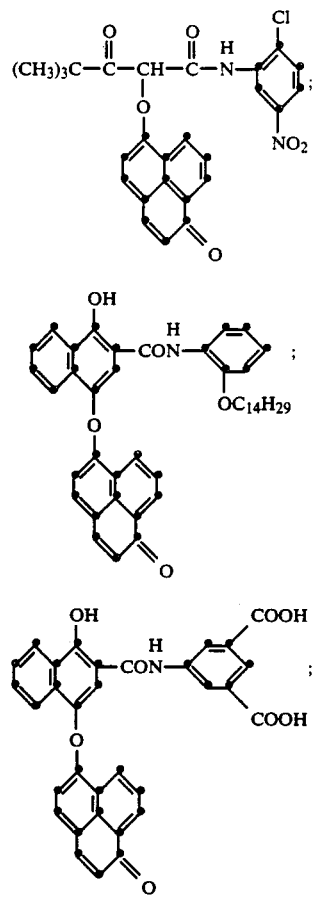

-continued

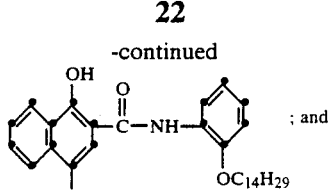

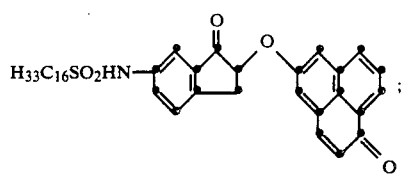

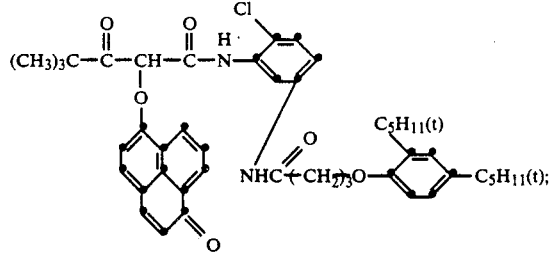

2. A method of detecting oxidase positive organisms comprising the steps of
   a) providing a reagent according to claim 1;
   b) providing a material capable of containing an oxidase positive organism and
   c) mixing an aliquot of a) with the material of b) thereby providing a color or fluorescence in the mixture if the oxidase positive organism is present.

3. An analytical element for detecting oxidase positive organisms in aqueous liquids comprising an absorbent material or a water soluble polymer containing a reagent according to claim 1.

* * * * *